(12) United States Patent
Boele et al.

(10) Patent No.: US 7,674,919 B2
(45) Date of Patent: Mar. 9, 2010

(54) PROCESS FOR THE PREPARATION OF ALKYLENE CARBONATE

(75) Inventors: Dirk Michiel Boele, Amsterdam (NL); Henricus Petrus Bernardus Duijghuisen, Amsterdam (NL); Eugene Marie Godfried Andre Van Kruchten, Amsterdam (NL); Jan Herman Hendrik Meurs, Amsterdam (NL)

(73) Assignee: Shell Oil Company, Houston, TX (US)

( * ) Notice: Subject to any disclaimer, the term of this patent is extended or adjusted under 35 U.S.C. 154(b) by 6 days.

(21) Appl. No.: 11/855,509

(22) Filed: Sep. 14, 2007

(65) Prior Publication Data

US 2008/0071096 A1 Mar. 20, 2008

(30) Foreign Application Priority Data

Sep. 15, 2006 (EP) .................. 06254805

(51) Int. Cl.
 *C07D 317/38* (2006.01)
 *C07C 31/20* (2006.01)
(52) U.S. Cl. .................. 549/230; 549/229; 568/858
(58) Field of Classification Search ................ 549/228, 549/229, 230; 568/858
 See application file for complete search history.

(56) References Cited

U.S. PATENT DOCUMENTS

| | | | | |
|---|---|---|---|---|
| 2,773,070 | A | * 12/1956 | Lichtenwalter et al. ..... | 549/230 |
| 2,993,908 | A | 7/1961 | Millikan .................. | 260/340.2 |
| 3,535,341 | A | 10/1970 | Emmons .................. | 260/340.2 |
| 3,535,342 | A | 10/1970 | Emmons .................. | 260/340.2 |
| 4,160,116 | A | 7/1979 | Mieno et al. ................ | 568/867 |
| 4,283,580 | A | 8/1981 | Odanaka et al. ............. | 568/858 |
| 4,307,256 | A | 12/1981 | Cipriani et al. ............. | 568/867 |
| 4,314,945 | A | 2/1982 | McMullen et al. ....... | 260/340.2 |
| 4,778,658 | A | 10/1988 | Nielsen ....................... | 422/111 |
| 4,786,741 | A | 11/1988 | Sachs ......................... | 549/230 |
| 4,982,021 | A | 1/1991 | Best et al. ................... | 568/867 |
| 5,023,345 | A | * 6/1991 | Harvey ....................... | 549/230 |
| 5,218,135 | A | 6/1993 | Buysch et al. .............. | 558/277 |
| 5,391,767 | A | 2/1995 | Mais et al. .................. | 549/229 |
| 5,488,184 | A | 1/1996 | Reman et al. ............... | 568/867 |
| 6,124,508 | A | 9/2000 | Van Kruchten ............ | 568/867 |
| 6,153,801 | A | 11/2000 | Van Kruchten ............ | 568/867 |
| 6,156,909 | A | 12/2000 | Kim et al. ................... | 549/230 |
| 6,160,130 | A | 12/2000 | Kim et al. ................... | 549/230 |
| 6,399,536 | B2 | 6/2002 | Kim et al. ................... | 502/169 |

FOREIGN PATENT DOCUMENTS

| | | |
|---|---|---|
| DE | 1543555 | 3/1975 |
| EP | 156449 | 10/1985 |
| EP | 776890 | 1/2001 |
| EP | 1034158 | 8/2003 |
| FR | 2644795 | 9/1990 |
| GB | 2085748 | 5/1982 |
| JP | 56092228 | 7/1981 |
| JP | 57106631 | 7/1982 |
| JP | 59013741 | 1/1984 |
| JP | 2001151711 | 6/2001 |
| JP | 2001151713 | 6/2001 |
| WO | WO9520559 | 8/1995 |
| WO | WO2005003113 | 1/2005 |

OTHER PUBLICATIONS

J. Catal (2002) 205, 226-229.
J. Catal (2003) 220, pp. 44-46.
Angew. Chem. Int Ed (2000) 39 (227), pp. 4096-4098.
Chem. Eur. J. (2003) 9(3), pp. 678-686.
Chem. Ber. (1986) 119, pp. 1090-1094.
Appl. Catal., A (2005) 275-pp. 125-129.
Chem. Commun (2006), pp. 1664-1666.
Kirk Othemer's Encyclopedia of Chemical Technology, 4$^{th}$ Edition, vol. 9, pp. 923-940.
Mai Tu et al., "Cycloaddition of $CO_2$ to Epoxides Over Solid Base Catalysts," *Journal of Catalysis*, Academic Press, Duluth, MN, US, vol. 199, Apr. 2001, pp. 85-91, XP004432595, ISSN: 0021-9517, Table 3 and first paragraph on p. 88.
Tadashi Sakai et al., "Polymer Reaction of Epoxide and Carbon Dioxide. Incorporation of Carbon Dioxide Into Epoxide Polymers," *Macromolecules*, vol. 28, No. 13, 1995, pp. 4701-4706, XP002419245, p. 4701, 2nd column, paragraph 2, p. 4702, 2nd column, paragraph 1.
Wing Nga Sit et al., "Coupling Reactions of $CO_2$ With Epoxides Catalyzed by PPN Salts to Yield Cyclic Carbonates," *J. Org. Chem.* Oct. 14, 2005, vol. 70, No. 21, pp. 8583-8586, XP002419247. ISSN: 0022-3263, 1st paragraph, 2nd column, p. 8583.
Alessandro Barbarini et al., "Cycloaddition of $CO_2$ to Epoxides Over Both Homogeneous and Silica-Supported Guanidine Catalysts," *Tetrahedron Letters*, Elsevier, Amnsterdam, NL, vol. 44, No. 14, (Mar. 31, 2003) pp. 2931-2934, XP004414426, ISSN: 0040-4039, p. 2931.
Jin-Wen Huang et al., "Chemical Fixation of Carbon Dioxide by NaI/PPh$_3$/ PhOh," *J. Org. Chem.*, Sep. 1, 2003, vol. 68, pp. 6705-6709, XP002419248, ISSN: 0022-3263, Table 2 in p. 6706.

* cited by examiner

*Primary Examiner*—Bernard Dentz

(57) ABSTRACT

A process for the preparation of an alkylene carbonate, said process comprising contacting the corresponding alkylene oxide with carbon dioxide in the presence of water and in the presence of a catalytic composition comprising an organic base neutralized with a hydrogen halide, wherein the organic base comprises a carbon-based compound comprising one or more nitrogen atoms with at least one free electron pair and/or one or more phosphorous atoms with at least one free electron pair and wherein the organic base has a $pK_a$ greater than 8.

20 Claims, No Drawings

PROCESS FOR THE PREPARATION OF ALKYLENE CARBONATE

CROSS-REFERENCE TO RELATED APPLICATIONS

This application claims the benefit of European Patent Application No. 06254805.2, filed Sep. 15, 2006, which is incorporated herein by reference in its entirety.

FIELD OF THE INVENTION

The invention relates to a process for the preparation of alkylene carbonate by the catalytic carboxylation of alkylene oxide.

BACKGROUND OF THE INVENTION

Alkylene carbonates, such as ethylene carbonate and propylene carbonate are widely used as solvents and diluents in industrial processes. They are regularly used as raw materials for commercial products such as cosmetics and pharmaceuticals. Alkylene carbonates can also be used as intermediates in the preparation of alkylene glycols from alkylene oxides.

Alkylene carbonates are produced commercially by the reaction of carbon dioxide with the appropriate alkylene oxide. In the art, ionic halides, such as quaternary ammonium halides, quaternary phosphonium halides and metal halides, are frequently proposed as catalysts for this reaction.

According to JP-A-57,106,631, the preparation of alkylene carbonate as an intermediate in the two-step preparation of alkylene glycol can occur by the reaction of an alkylene oxide with carbon dioxide in the presence of an alkali metal halide.

U.S. Pat. No. 4,314,945 is directed to the preparation of an alkylene carbonate by reaction of the corresponding alkylene oxide with carbon dioxide in the presence of a catalyst characterized by the formula $M^+A^-$, wherein M is potassium and A is iodine or M is a quaternary ammonium cation $(R^1R^2R^3R^4N^+)$ and A is either bromine, chlorine or iodine. The reaction is carried out in alkylene carbonate.

U.S. Pat. No. 4,786,741 is directed to the reaction of alkylene oxides with carbon dioxide in the presence of a catalytic composition and water. Catalytic compositions listed include organic quaternary ammonium halides, organic quaternary phosphonium halides, organic sulphonium halides and organic antimony halides.

JP-A-59,013,741 teaches a method for producing ethylene glycol from ethylene oxide via ethylene carbonate. The reaction of ethylene oxide with carbon dioxide to form ethylene carbonate is catalysed with a quaternary phosphonium halide.

The use of a combination of an alkali metal halide and manganese halide as a catalyst for the preparation of alkylene carbonates from alkylene oxides has been described in U.S. Pat. No. 6,160,130. Lead and indium halides in combination with an alkali metal halide are taught as suitable catalysts for this reaction in U.S. Pat. No. 6,156,909.

Kim et al. have described the use of zinc halides in combination with various other compounds as effective catalysts for the carboxylation of alkylene oxides. In *J. Catal.* (2003) 220, 44-46, a catalyst formed by the reaction of 1-alkyl-3-methylimidazolium halides with zinc halides is described. Catalysts comprising zinc halides coordinated with pyridines are described in *Angew. Chem. Int. Ed.* (2000) 39(22), 4096-4098, *Chem. Eur. J.* (2003) 9(3), 678-686 and U.S. Pat. No. 6,399,536.

Mixtures of zinc halides and alkylammonium iodides as catalysts for the conversion of alkylene oxides to alkylene carbonates are taught in *Chem. Ber.* (1986) 119, 1090-1094.

Homogeneous catalysts composed of one of a number of metal salts in combination with a halide selected from the group of alkali metal halides, alkaline earth metal halides, quaternary ammonium, quaternary phosphonium, quaternary arsenonium, quaternary stibonium halides and ternary sulphonium halides have been described for use in the conversion of alkylene oxides to alkylene carbonates in U.S. Pat. Nos. 5,218,135 and 5,391,767.

The application of acid salts of hydrazine and guanidine as catalysts for the reaction of an alkylene oxide with $CO_2$ under superatmospheric pressure is described in U.S. Pat. Nos. 3,535,341 and 3,535,342, respectively. Halide salts of ureas have also been reported as catalysts for this reaction in U.S. Pat. No. 2,993,908. DE-A-1,543,555 teaches the uses of derivatives of carbamic acids, particularly the stable salts of the basic derivatives of carbamic acids, for the conversion of alkylene oxide to alkylene carbonate.

Heterogeneous catalysts for the carboxylation of propylene oxide to propylene carbonate, consisting of quaternary phosphonium halides immobilized on silica, were reported by Takahashi, et al. in *Chem. Commun.* (2006) 1664-1666.

A solid-supported zinc halide, wherein the solid support is poly(4-vinylpyridine) is described by Kim et al. in *J. Catal.* (2002) 205, 226-229. However, this system is described as having reduced activity in comparison to the equivalent homogeneous system.

A solid-supported system based on zinc halide, wherein the solid support is either poly(4-vinylpyridine) or chitosan is described by Xiao et al. in *Appl. Catal., A* (2005) 275, 125-129. A homogeneous 1-butyl-3-methylimidazolium bromide co-catalyst must also be used in this system.

Even after the advances described above, there still remains a need for the development of improved catalyst systems for the conversion of alkylene oxide to alkylene carbonate, which demonstrate high levels of selectivity and activity. Further, catalysts capable of being used in a heterogeneous system and thus allowing facile separation of the product alkylene carbonate are also desired.

SUMMARY OF THE INVENTION

The present invention provides a process for the preparation of an alkylene carbonate, said process comprising contacting the corresponding alkylene oxide with carbon dioxide in the presence of water, wherein the amount of water is at least 0.05 mol/mol alkylene oxide, and in the presence of a catalytic composition comprising an organic base neutralized with a hydrogen halide, wherein the organic base comprises a carbon-based compound comprising one or more nitrogen atoms with at least one free electron pair and/or one or more phosphorous atoms with at least one free electron pair and wherein the organic base has a $pK_a$ greater than 8.

Also provided by the present invention is a process for the preparation of an alkylene carbonate, said process comprising contacting the corresponding alkylene oxide with carbon dioxide in the presence of water, wherein the amount of water is least 0.05 mol/mol alkylene oxide, and in the presence of a catalytic composition comprising an organic base neutralized with a hydrogen halide, wherein the organic base comprises a carbon-based compound comprising one or more nitrogen atoms with at least one free electron pair and/or one or more phosphorous atoms with at least one free electron pair and wherein the organic base has a $pK_a$ greater than 8, wherein the catalytic composition is immobilized on a solid support.

DETAILED DESCRIPTION OF THE INVENTION

We have now found that the conversion of alkylene oxide to alkylene carbonate in the presence of carbon dioxide and water can be efficiently catalysed by a range of compositions comprising organic bases, with a $pK_a$ greater 8, neutralized with a hydrogen halide.

Such catalytic compositions of the present invention provide excellent levels of selectivity and activity in the conversion of alkylene oxide to alkylene carbonate. Catalytic compositions according to the present invention may also be immobilized on a solid support in order to provide a heterogeneous catalyst system, thus allowing a simplified process during the separation and purification of the intended product, whilst retaining or improving on the high activity and selectivity demonstrated by the homogeneous equivalents.

The alkylene oxide used as starting material in the process of the invention has its conventional definition, i.e. a compound having a vicinal oxide (epoxy) group in its molecules.

Particularly suitable are alkylene oxides of the general formula (I),

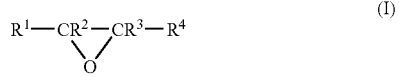

wherein $R^1$ to $R^4$ independently represent a hydrogen atom or an optionally substituted alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, and 2,3-epoxybutane. In the present invention, the most preferred alkylene oxide is ethylene oxide.

Alkylene oxide preparation is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, 4$^{th}$ edition, Vol. 9, pages 923-940).

As used herein, the term alkylene carbonate refers to a five-membered alkylene carbonate (1,3-dioxolan-2-ones) of the general formula (II),

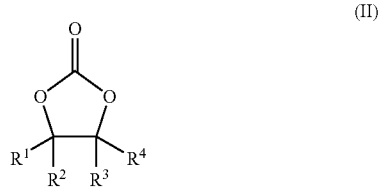

wherein $R^1$ to $R^4$ correspond to $R^1$ to $R^4$ of the parent alkylene oxide. Therefore, suitable alkylene carbonates include ethylene carbonate, propylene carbonate, 1,2-butylene carbonate, and 2,3-butylene carbonate. In the present invention, the most preferred alkylene carbonate of the general formula (II) is ethylene carbonate, where $R^1$, $R^2$, $R^3$ and $R^4$ all represent hydrogen atoms.

Organic bases according to the present invention are carbon-based compounds also containing one or more nitrogen and/or phosphorous atoms which have at least one free electron pair. The organic base has a $pK_a$ greater than 8. Suitable organic bases include, but are not limited to, amines, hydroxylamines, hydrazines, hydrazones, amidines, amidrazones, hydrazidines, formazans, carbodiimides, guanidines, ureas, cyanamides, pyridines, pyrimidines, quinolines, imidazoles, triazoles, phosphazenes, phosphines, imines, and imides. Preferably, the organic base is selected from the group comprising phosphazenes, amines, pyridines, and guanidines.

Preferably, the hydrogen halide used to form the catalytic composition of the present invention is selected from hydrogen fluoride, hydrogen chloride, hydrogen bromide, and hydrogen iodide. Most preferably, the hydrogen halide is hydrogen iodide.

Suitably, the organic base is neutralized with the hydrogen halide in an aqueous solution before addition of the alkylene oxide.

In a preferred embodiment of the present invention, the catalytic composition comprising an organic base neutralized with a hydrogen halide is immobilized on a solid support. Typically, in this embodiment, the organic base will be immobilized on the solid support before addition of the hydrogen halide. Solid supports suitable for use in the process of the present invention include those of an inorganic nature such as carbon, silica, silica-alumina, zeolites, glass and clays. Such solid supports may have the neutralized organic base bonded by adsorption, reaction or grafting. Advantageously, in the present invention, solid supports comprising a polymeric backbone are used. The polymeric backbone may comprise high molecular weight polymers and co-polymers including polyalkylene, polyester, polycarbonate, polyurethane, formaldehyde resins, etc. Silica-based polymeric backbones, such as polysiloxanes may also be used. Weakly basic ion exchange resins, for example REILLEX 402 (polyvinylpyridine), are also suitable (REILLEX is a trade mark).

The term neutralized when used herein refers to the organic base and hydrogen halide having been reacted together in amounts relative to each other such that an aqueous solution of the product formed has a pH in the range of from 6 to 8, preferably in the range of from 6.5 to 7.5, most preferably in the range of from 6.9 to 7.1. The pH of such a solution can be measured by any of the methods well known in the art, such as by using a standard pH meter or indicator paper.

In the case of solid supported organic bases, wherein an aqueous solution of the base cannot be formed, sufficient hydrogen halide should be added to the solid supported base in water so that the hydrogen halide is present in at least a 1:1 ratio of hydrogen halide to the number of basic centres present in the supported organic base. The number of basic centres present in a specific amount of a particular solid-supported organic base can easily be calculated by one skilled in the art based on the number of basic centres in an individual molecule of the organic base, the density of the organic base molecules on the solid support and the amount of the solid-supported organic base compound used. If too much hydrogen halide is added, the pH of the aqueous solution surrounding the solid catalyst will fall below 6. Excess hydrogen halide can then be washed away by repeatedly washing the catalytic composition with deionized water until the wash water has a pH in the range of from 6 to 8, preferably in the range of from 6.5 to 7.5.

Preferably, the total amount of carbon dioxide supplied to the reactor in which the process of the present invention is carried out is an amount of at least 0.5 mol/mol alkylene oxide, preferably at least 1 mol/mol alkylene oxide. Preferably, the total amount of carbon dioxide supplied to the reactor is an amount of at most 100 mol/mol alkylene oxide, more preferably in an amount of at most 10 mol/mol alkylene oxide.

The alkylene oxide used in the process of the present invention may comprise purified alkylene oxide or any other suitable alkylene oxide. For example, the alkylene oxide used in the process of the present invention may comprise alkylene oxide from a commercial alkylene oxide plant after it has undergone one or more purification treatments, for example by distillation.

The amount of water present is at least 0.05 mol/mol alkylene oxide present in the reaction mixture, preferably at least 0.1 mol/mol alkylene oxide. An amount of water present of at least 0.2 mol/mol alkylene oxide is most preferred. Preferably, the amount of water present is less than 10 mol/mol alkylene oxide, more preferably less than 5 mol/mol of alkylene oxide. An amount of water present of at most 2 mol/mol alkylene oxide is most preferred. Very suitably an amount of water in the range of from 0.5 to 2 mol/mol alkylene oxide is used.

It is a further benefit of the present invention that a close to stoichiometric amount of water to alkylene oxide, for example an amount of water in the range of from 1 mol/mol alkylene oxide to 1.3 mol/mol alkylene oxide, is particularly suitable for the process of the present invention. The use of this amount of water provides excellent activity and reaction rate. Further, if the product alkylene carbonate is subsequently to be converted into the corresponding alkylene glycol, a suitable amount of water is already present in the reaction mixture.

The water present in the reaction mixture of the present invention may be added to the reaction mixture separately from the alkylene oxide. For example, the water may be added to the reaction mixture in the form of an aqueous solution of the catalytic composition. This has the benefit that the catalytic composition can be formed by neutralisation of the organic base with the hydrogen halide in water and the resultant solution of the catalytic composition can then be added to the reaction mixture with no further purification. Alternatively, the alkylene oxide and some or all of water may be pre-mixed before being supplied to the reactor. In a preferred embodiment of the invention, an alkylene oxide product mixture from an alkylene oxide reactor is used either without further process steps or after some concentration in a stripper. Most preferably, an ethylene oxide/water mixture, formed by absorption with water of the product stream from a direct oxidation ethylene oxide reactor is used. This method has a further benefit that the energy expended in isolating the alkylene oxide, prior to the process of the invention, is reduced.

Suitably, the catalytic composition comprising an organic base neutralized with a hydrogen halide is present in amount in the range of from 0.0001 to 0.5 mol/mol alkylene oxide (based on the halide). Preferably, the catalytic composition is present in an amount in the range of from 0.001 to 0.1 mol/mol alkylene oxide (based on the halide).

The process of the present invention can be carried out in any reaction system suitable for a carboxylation process.

The process of the present invention may be carried out in batch operation. However, in particular for large-scale embodiments, it is preferred to operate the process continuously.

When using an immobilized catalyst, such continuous process can be carried out in fixed bed reactors, operated in up-flow or down-flow. Other reactor options include bubble column reactors (suitable for use with both immobilized and homogeneous catalysts) and fluidized bed reactors (suitable for use with immobilized catalysts).

The reactors of the present invention may be maintained under isothermal, adiabatic or hybrid conditions. Isothermal reactors are generally shell- and tube reactors, mostly of the multi-tubular type, wherein a coolant passes outside the tubes and the tubes contain either a reaction mixture including a homogeneous catalyst, or a reaction mixture, which passes over an immobilized catalyst that is retained inside the tubes. Adiabatic reactors are not cooled, and the product stream leaving them may be cooled in a separate heat exchanger.

It may be advantageous for the process of this invention to recycle a part of the reactor output to at least one inlet of the same reactor, because any temperature difference that may arise between the top and the bottom of the reactor is minimized. Accordingly, less external temperature control is required to maintain the reaction temperature than with a conventional reactor. This is particularly advantageous when isothermal conditions are preferred. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed. The amount of reactor output mixture to be recycled may be varied to obtain optimum performance with regard to other reaction parameters employed.

In order to accommodate any swelling of the catalyst that may occur during operation when using an immobilized catalyst, the reactor volume can advantageously be greater than the volume occupied by the catalyst therein, for example 10 to 70 vol % greater.

Suitable reaction temperatures for the catalytic carboxylation of alkylene oxides, according to the present invention, are generally in the range of from 40 to 200° C.; temperatures in the range of from 50 to 120° C. are preferred.

The reaction pressure is usually selected in the range of from 100 to 5000 kPa, preferably in the range of from 200 to 3000 kPa, most preferably in the range of from 500 to 2000 kPa.

The product alkylene carbonate may find use in any of the applications well known for this class of chemicals. Alternatively, the product alkylene carbonate may be subject to further chemical transformations in order to form other products. In one embodiment of the present invention, the alkylene carbonate that is the product of the process of the present invention is then subjected to a hydrolysis step in order to form the corresponding alkylene glycol.

A problem, which may occasionally arise in certain processes using nitrogen- and or phosphorous-containing catalytic compositions, is the presence of small amounts of amines and/or phosphines as impurities in the product stream. It has been found that during operation, small amounts of amines and/or phosphines may leach from immobilized catalysts into the product stream. When a homogeneous catalyst composition is used, amines and/or phosphines may also remain in the product stream after removal of the catalyst. Besides, amines in the product stream may also originate from corrosion inhibitors, which may be added to the water used in the process. Although the amounts of such amine and/or phosphine contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odour of TMA may be detected in an amount as low as 1 ppb.

An effective measure in removing such amines and/or phosphines is the use of a post-reactor bed, containing an acidic species, particularly a strongly acidic ion exchange resin, which effectively captures the amines and/or phosphines. When using an immobilized homogeneous catalyst, such a post-reactor bed may be positioned directly after the reactor bed. However, when using a non-immobilized, homogeneous catalyst, the post-reactor bed should be used to treat the product stream after removal of the homogeneous catalyst. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB, and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product stream after passing it may become acidic. Using a mixture of the strongly acidic ion exchange resin in its $H^+$ form and salt form has the advantage of the pH of the product stream remaining close to neutral.

Such a post-reactor bed may be positioned after a carboxylation reaction bed in which the process according to the present reaction is carried out. Alternatively, the post-reactor bed may be placed after a subsequent reactor or series of reactors in which the product alkylene carbonate has undergone further chemical transformations, such as hydrolysis to the corresponding glycol. An added advantage of the strongly acidic post-reactor bed positioned after a reactor bed in which the alkylene carbonate has undergone hydrolysis to form the corresponding alkylene glycol is that any remaining alkylene carbonate, which may be still present in the product alkylene glycol product stream, is hydrolysed to alkylene glycol.

In order to allow for exhaustion of the strongly acidic ion exchange resin during operation, it is advantageous to operate the post-reactor bed in two or more separate vessels, to allow the process to be switched between the two vessels, thus maintaining continuous operation.

Exhausted strongly acidic ion exchange resin can be regenerated by treatment with an acid, such as HCl and $H_2SO_4$. Hot sulfuric acid of 0.1 to 2 N has been proven to be effective.

Having generally described the invention, a further understanding may be obtained by reference to the following examples, which are provided for purposes of illustration only and are not intended to be limiting unless otherwise specified. The following Examples will illustrate the invention.

EXAMPLES

The abbreviations used herein have the following definitions:

| TMG | 1,1,3,3-tetramethylguanidine |
| P1 | 2-tert-butylimino-2-diethylamino-1,3-dimethyl-perhydro-1,3,2-diazaphosphorin (a phosphazene) |
| TEA | tri-ethanolamine |
| P1-POL | 2-tert-butylimino-2-diethylamino-1,3-dimethyl-perhydro-1,3,2-diazaphosphorin on polystyrene |
| TBPMI | methyltributylphosphonium iodide |

The catalyst compositions were produced using the following methods:

Catalyst 1: TMG-hydroiodide 1,1,3,3-tetramethylguanidine (0.99 g, 8.6 mmol) was dissolved in approximately 15 g of water. A solution (57 wt %) of hydroiodic acid (1.9 g, 8.5 mmol) was added slowly. The pH was measured to ensure that it was approximately 7. A further 7 g of water was added in order to provide a 0.34M catalyst solution.

Catalyst 2: P1-hydroiodide 2-tert-butylimino-2-diethylamino-1,3-dimethyl-perhydro-1,3,2-diazaphosphorin (2.41 g, 8.8 mmol) was dissolved in approximately 15 g of water. A solution (57 wt %) of hydroiodic acid (1.95 g, 8.8 mmol) was added slowly. The pH of the solution was measured to ensure that it was approximately 7. A further 5.6 g of water was added in order to provide a 0.35M catalyst solution.

Catalyst 3: TEA-hydroiodide

Tri-ethanolamine (1.31 g, 8.8 mmol) was dissolved in approximately 15 g of water. A solution (57 wt %) of hydroiodic acid (1.9 g, 8.5 mmol) was added slowly. The pH of the solution was measured to ensure that it was approximately 7. A further 6.8 g of water was added in order to provide a 0.34M catalyst solution.

Catalyst 4: P1-POL-hydroiodide 2-tert-butylimino-2-diethylamino-1,3-dimethyl-perhydro-1,3,2-diazaphosphorin on polystyrene (4.1 g, 2.2 mmol base/g) was combined with approximately 15 g of water. A solution (57 wt %) of hydroiodic acid (1.95 g, 8.8 mmol) was added slowly. The pH of the solution was measured to ensure that it was approximately 7. A further 4 g of water was added in order to provide a 0.35M catalyst composition (based on 2.2 mmol phosphazene base/g).

The following carboxylation reactions were all carried out in a 125 ml Medimex autoclave according to the following procedures. TBPMI was used as a comparative catalyst.

General Reaction Procedure

The reactor was filled with water and the catalyst composition, in the amounts shown in Table 1. The reactor was then purged with $CO_2$ and pressurized with a $CO_2$ atmosphere of approximately 5 bar (500 kPa). The reactor content was then heated to 80° C. and the reactor was further pressurized to 20 bar (2,000 kPa). The ethylene oxide was then pumped into the reactor at a rate of 6.0 g/min until the amount given in Table 1 was reached. The reactor content was maintained at the above temperature and pressure (by the continuous supply of $CO_2$) and samples were taken at regular time intervals and analysed by gas liquid chromatography (GLC). The results of these Examples are shown in Table 2.

TABLE 1

| Catalyst | Amount (mmol) | Water (g) | Ethylene oxide (mmol) |
| --- | --- | --- | --- |
| TBPMI (comparative) | 9.1 | 24.6 | 0.756 |
| 1: TMG-hydroiodide | 8.3 | 22.9 | 0.756 |
| 2: P1-hydroiodide | 8.8 | 20.6 | 0.756 |
| 3: TEA-hydroiodide | 8.7 | 22.3 | 0.756 |
| 4: P1POL-hydroiodide | 8.6 | 19.3 | 0.756 |

TABLE 2

| Catalyst | EO conv. (60 min) (%) | Selectivity (60 min) | | | TOF* (h⁻¹) |
| --- | --- | --- | --- | --- | --- |
| | | EC (%) | MEG (%) | Total (%) | |
| TBPMI (comparative) | 79 | 95.3 | 4.6 | 99.9 | 65 |
| 1: TMG-hydroiodide | 69 | 94.7 | 5.2 | 99.8 | 63 |
| 2: P1-hydroiodide | 76 | 95.0 | 4.9 | 99.9 | 65 |
| 3: TEA-hydroiodide | 43 | 91.4 | 8.3 | 99.7 | 37 |
| 4: P1POL-hydroiodide | 86 | 98.0 | 1.9 | 99.9 | 76 |

*TOF = Turn over frequency (moles of EC produced/mole of catalyst/h;

As is shown in Table 2, good levels of activity and selectivity have been achieved with the catalysts of the present invention.

Particularly impressive results have been demonstrated by the P1 catalyst immobilized on a solid support (P1POL-hydroiodide), which provides excellent levels of selectivity both to the ethylene carbonate and in total, as well as a high activity (TOF). Such a heterogeneous catalyst also allows facile purification of the alkylene carbonate from the catalyst. The aqueous reaction mixture, separated from the heterogeneous catalyst by a simple method, such as filtration, may then be used directly in a further transformation, e.g. hydrolysis of the carbonate to the glycol without any further purification or addition of energy.

What is claimed is:

1. A process for the preparation of an alkylene carbonate, said process comprising contacting the corresponding alkylene oxide with carbon dioxide in the presence of water, wherein the amount of water is at least 0.05 mol/mol alkylene oxide, and in the presence of a catalytic composition comprising an organic base neutralized with a hydrogen halide, wherein the organic base comprises a carbon-based compound comprising one or more nitrogen atoms with at least one free electron pair and/or one or more phosphorous atoms with at least one free electron pair, and wherein the organic base has a $pK_a$ greater than 8.

2. The process as claimed in claim 1, wherein the catalytic composition is immobilized on a solid support.

3. The process as claimed in claim 2, wherein the solid support comprises a polymeric backbone.

4. The process as claimed in claim 1, wherein the organic base is selected from the group consisting of amines, hydroxylamines, hydrazines, hydrazones, amidines, amidrazones, hydrazidines, formazans, carbodiimides, guanidines, ureas, cyanamides, pyridines, pyrimidines, quinolines, imidazoles, triazoles, phosphazenes, phosphines, imines, and imides.

5. The process as claimed in claim 1, wherein the organic base is selected from the group consisting of amines, phosphazenes, pyridines, and guanidines.

6. The process as claimed in claim 1, wherein the hydrogen halide is selected from the group consisting of hydrogen fluoride, hydrogen chloride, hydrogen bromide, and hydrogen iodide.

7. The process as claimed in claim 1, wherein the hydrogen halide is hydrogen iodide.

8. The process as claimed in claim 1, wherein the molar ratio of catalyst to alkylene oxide is in the range of from 0.0001 to 0.5 mol/mol (based on the halide).

9. The process as claimed in claim 1, wherein the molar ratio of catalyst to alkylene oxide is in the range of from 0.001 to 0.1 mol/mol (based on the halide).

10. The process as claimed in claim 1, wherein the process takes place at a temperature in the range of from 40 to 200° C. and at a pressure in the range of from 100 to 5000 kPa.

11. The process as claimed in claim 1, wherein water is present in an amount in the range of from at least 0.1 to less than 10 mol/mol alkylene oxide present in the reaction mixture.

12. The process as claimed in claim 1, wherein water is present in an amount in the range of from 0.5 to 2 mol/mol alkylene oxide present in the reaction mixture.

13. The process as claimed in claim 1, wherein carbon dioxide is present in an amount in the range of from 0.5 to 100 mol/mol alkylene oxide present in the reaction mixture.

14. The process as claimed in claim 1, wherein carbon dioxide is present in an amount in the range of from 1 to 10 mol/mol alkylene oxide present in the reaction mixture.

15. The process as claimed in claim 1, wherein the alkylene oxide is ethylene oxide.

16. A process for the preparation of ethylene carbonate, said process comprising contacting ethylene oxide with carbon dioxide in the presence of water, wherein the amount of water is at least 0.05 mol/mol ethylene oxide, and in the presence of a catalytic composition comprising an organic base neutralized with hydrogen iodide, wherein the organic base is selected from the group consisting of amines, phosphazenes, pyridines, and guanidines, and wherein the organic base has a $pK_a$ greater than 8.

17. The process as claimed in claim 16, wherein the catalytic composition is immobilized on a solid support which comprises a polymeric backbone.

18. The process as claimed in claim 16, wherein water is present in an amount in the range of from 1 to 1.3 mol/mol ethylene oxide present in the reaction mixture.

19. A process for the preparation of an alkylene glycol comprising preparing an alkylene carbonate by the process according to claim 1, and then hydrolyzing the alkylene carbonate to form the corresponding alkylene glycol.

20. A process for the preparation of ethylene glycol comprising preparing ethylene carbonate by the process according to claim 16, and then hydrolyzing the ethylene carbonate to form ethylene glycol.

* * * * *